(12) United States Patent
Ichikawa et al.

(10) Patent No.: US 8,827,914 B2
(45) Date of Patent: Sep. 9, 2014

(54) FUNCTION ADDING MODULE

(75) Inventors: Tsutomu Ichikawa, Kyoto (JP); Takahide Tanaka, Otsu (JP)

(73) Assignee: Omron Healthcare Co., Ltd., Kyoto (JP)

(*) Notice: Subject to any disclaimer, the term of this patent is extended or adjusted under 35 U.S.C. 154(b) by 557 days.

(21) Appl. No.: 13/230,181

(22) Filed: Sep. 12, 2011

(65) Prior Publication Data
US 2011/0319770 A1 Dec. 29, 2011

Related U.S. Application Data

(63) Continuation of application No. PCT/JP2010/051939, filed on Feb. 10, 2010.

(30) Foreign Application Priority Data

Mar. 12, 2009 (JP) ................................. 2009-059254

(51) Int. Cl.
*A61B 5/022* (2006.01)
*A61B 5/021* (2006.01)

(52) U.S. Cl.
CPC ............. *A61B 5/022* (2013.01); *A61B 5/02141* (2013.01)
USPC .......................................... 600/490; 600/485

(58) Field of Classification Search
USPC .................................................. 600/485–499
See application file for complete search history.

(56) References Cited

U.S. PATENT DOCUMENTS

| 6,450,966 B1* | 9/2002 | Hanna ............................ 600/490 |
| 7,316,651 B2* | 1/2008 | Yang et al. ..................... 600/490 |
| 8,123,694 B2* | 2/2012 | Kinsley et al. ................. 600/492 |
| 2003/0181816 A1* | 9/2003 | Shirasaki ....................... 600/490 |
| 2004/0077958 A1 | 4/2004 | Kato et al. |
| 2006/0122518 A1* | 6/2006 | Machit et al. .................. 600/490 |
| 2006/0293601 A1* | 12/2006 | Lane et al. ..................... 600/495 |
| 2008/0077021 A1* | 3/2008 | Ferber et al. ................... 600/485 |

FOREIGN PATENT DOCUMENTS

| EP | 1388319 A1 | 2/2004 |
| JP | 61-029333 A | 2/1986 |
| JP | 02060633 A | 3/1990 |
| JP | 04-158833 A | 6/1992 |
| JP | 06-038935 A | 2/1994 |
| JP | 07-008464 A | 1/1995 |
| JP | 08000580 A | 1/1996 |
| JP | 10-314132 A | 12/1998 |
| JP | 2002-034937 A | 2/2002 |
| JP | 2003102693 A | 4/2003 |
| WO | 02/39893 A1 | 5/2002 |

OTHER PUBLICATIONS

International Search Report issued in PCT/JP2010/051939 mailed on Mar. 9, 2010 with English translation thereof, 2 pages.

(Continued)

*Primary Examiner* — Jacqueline Cheng
*Assistant Examiner* — Eric Messersmith
(74) *Attorney, Agent, or Firm* — Osha Liang LLP

(57) ABSTRACT

A function adding module includes a connection portion for connection to an existing blood pressure meter with an air tube and a connection portion for connection to a cuff with an air tube. The function adding module calculates a pressure value by detecting a change in internal pressure of the cuff using an embedded pressure sensor. The function adding module has a memory function and stores the calculated blood pressure value in a memory.

6 Claims, 11 Drawing Sheets

(56) References Cited

OTHER PUBLICATIONS

Patent Abstracts of Japan, Publication No. 02-060633, Publication Date: Mar. 1, 1990, 1 page.
Patent Abstracts of Japan, Publication No. 2002-034937, Publication Date: Feb. 5, 2002, 1 page.
Patent Abstracts of Japan, Publication No. 08-000580, Publication Date: Jan. 9, 1996, 1 page.
Patent Abstracts of Japan, Publication No. 2003-102693, Publication Date: Apr. 8, 2003, 1 page.
Office Action issued in corresponding Chinese Application No. 201080011762.1 dated Apr. 24, 2013, and English translation thereof (15 pages).

* cited by examiner

FUNCTION ADDING MODULE

TECHNICAL FIELD

This invention relates to a function adding module, and more particularly, to a function adding module connected to an electronic blood pressure meter.

BACKGROUND ART

As a conventional electronic blood pressure meter, a simple one having functions of only measuring blood pressure and displaying the result thereof on an indicator was mainstream. As research on blood pressure management has progressed, an electronic blood pressure meter having a function of storing long-term measurement values for each member of a family and a function of automatically analyzing a tendency of blood pressure values has been developed.

SUMMARY OF INVENTION

There may be cases where there is a demand from a user who owns a conventional simple electronic blood pressure meter for adding a newly developed function as described above. In order to add such a function to an existing simple electronic blood pressure meter, as an example, causing an electronic blood pressure meter to include a structure for adding functions such as a connector or programs in advance has been considered.

However, in practice, the demand for adding a function to the simple electronic blood pressure meter occurs after the electronic blood pressure meter is purchased, such that the above structure cannot be later added to the existing simple electronic blood pressure meter. In this case, a high functional electronic blood pressure meter has to be newly acquired.

Therefore, one or more embodiments of the invention provide a function adding module that is connected to an electronic blood pressure meter to add a function.

According to one or more embodiments of the invention, a function adding module which is a module for connection to an electronic blood pressure meter includes: a first connection portion for connecting a first air tube; a second connection portion for connecting a second air tube; a pressure sensor connected to an air passage including the first and second connection portions; a calculation unit for, in a state where the air passage is connected to the electronic blood pressure meter at least with the first air tube interposed therebetween and is connected to an air bag at least with the second air tube interposed therebetween, on the basis of a change in internal pressure of the air bag detected by the pressure sensor, calculating a blood pressure value of a person to be measured to whom the air bag is mounted; and a storage unit for storing the calculated blood pressure value.

According to one or more embodiments of the present invention, the function adding module further includes a first determination unit for, in the state where the air passage is connected to the electronic blood pressure meter at least with the first air tube interposed therebetween and is connected to the air bag at least with the second air tube interposed therebetween, on the basis of the change in the internal pressure of the air bag detected by the pressure sensor, in a period of the change in the internal pressure of the air bag, determining a period used for calculating the blood pressure value by the electronic blood pressure meter, and the calculation unit calculates the blood pressure value, in the state where the air passage is connected to the electronic blood pressure meter at least with the first air tube interposed therebetween and is connected to the air bag at least with the second air tube interposed therebetween, on the basis of the change in the internal pressure in the determined period from the change in the internal pressure of the air bag detected by the pressure sensor.

According to one or more embodiments of the present invention, in a case where an amount of the change in the internal pressure of the air bag is in a predetermined range stored in advance, the first determination unit determines that the period of the change in the internal pressure is the period used for calculating the blood pressure value by the electronic blood pressure meter.

According to one or more embodiments of the present invention, the function adding module further includes a second determination unit which, in the state where the air passage is connected to the electronic blood pressure meter at least with the first air tube interposed therebetween and is connected to the air bag at least with the second air tube interposed therebetween, on the basis of patterns of the change in the internal pressure of the air bag detected by the pressure sensor and a change in the internal pressure of the air bag stored to be associated with the electronic blood pressure meter in advance, determines whether or not the electronic blood pressure meter connected with the interposed first air tube is an electronic blood pressure meter stored in advance, and the calculation unit calculates the blood pressure value on the basis of the change in the internal pressure of the air bag detected by the pressure sensor, in the state where the air passage is connected to the electronic blood pressure meter stored in advance at least with the first air tube interposed therebetween and is connected to the air bag at least with the second air tube interposed therebetween.

According to one or more embodiments of the present invention, the storage unit includes a storage area corresponding to a subject, the function adding module further includes operation units for receiving an operation of designating the subject to whom the air bag is mounted, and the storage unit stores the calculated blood pressure value in the storage area corresponding to the designated subject.

According to one or more embodiments of the present invention, the function adding module further includes: a power supply for supplying power to the function adding module; and a control unit for, in a case where the change in the internal pressure of the air passage detected by the pressure sensor is equal to or greater than a predetermined amount stored in advance, performing control to supply the power to the function adding module from the power supply.

According to one or more embodiments of the present invention, the function adding module further includes: a third connection portion for electrical connection to an external device; and an output for outputting information stored in the storage unit to the external device connected to the third connection portion.

According to one or more embodiments of the invention, by connecting an existing electronic blood pressure meter to an air tube, a function can be added to the existing electronic blood pressure meter.

DETAILED DESCRIPTION OF INVENTION

Figure 1:
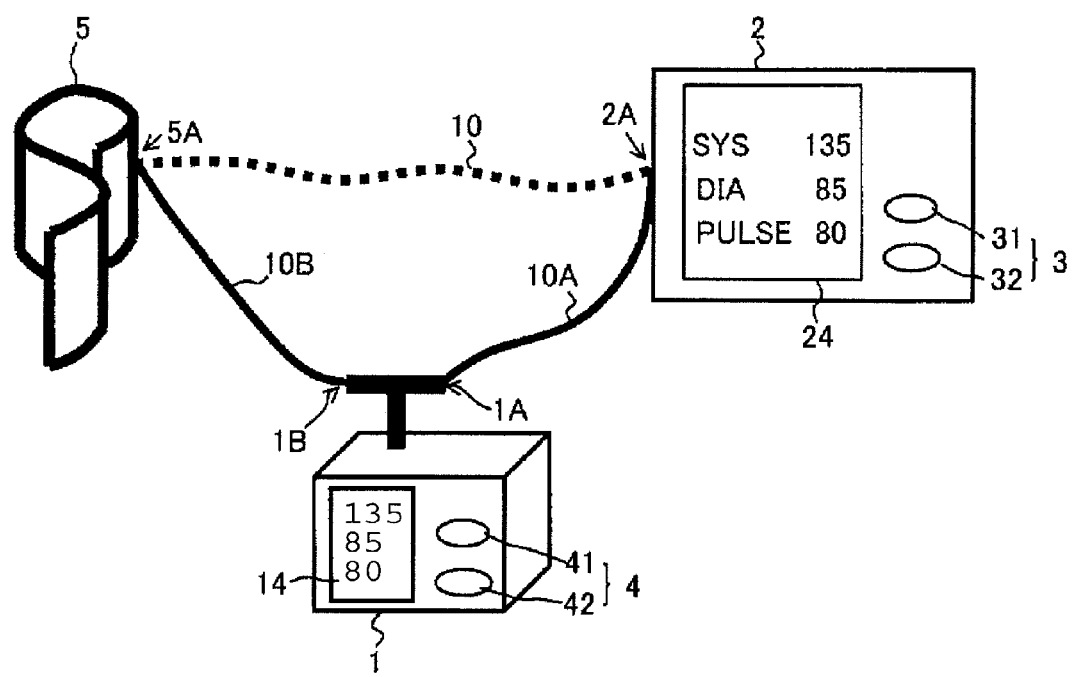
FIG. 1 is a diagram for explaining a connection of a function adding module (hereinafter, abbreviated to a module) to a blood pressure meter according to one or more embodiments of the present invention.

Hereinafter, embodiments of the invention will be described with reference to the drawings. In the following description, like components and elements are denoted by like reference numerals. This is also applied to names and functions.

Referring to FIG. 1, a function adding module (hereinafter, abbreviated to a module) 1 according to one or more embodiments of the present invention is connected to a blood pressure meter 2, which is an existing electronic blood pressure meter with an air tube 10A, and is connected to a cuff 5 including an air bag 51 (see FIG. 4) therein with an air tube 10B.

When the blood pressure meter 2, which is a single body, performs blood pressure measurement, the blood pressure meter 2 and the air bag 51 are connected with an air tube 10. The blood pressure meter 2 and the air bag 51 have connection portions 2A and 5A, respectively, for connection to the air tube 10. The module 1 includes a connection portion 1A for connection to the blood pressure meter 2 and a connection portion 1B for connection to the cuff 5. The connection portions 1A and 1B have the same shapes as those of the connection portions 2A and 5A. Therefore, as air tubes 10A and 10B, air tubes having the same shape as that of the air tube 10 can be used.

On the front surface of the module 1, a display unit 14 that displays measurement results and the like, and an operation unit 4, which includes a switch 41 for instructing powering on and off and a switch 42 for instructing execution of computation described below, are disposed.

Figure 2:
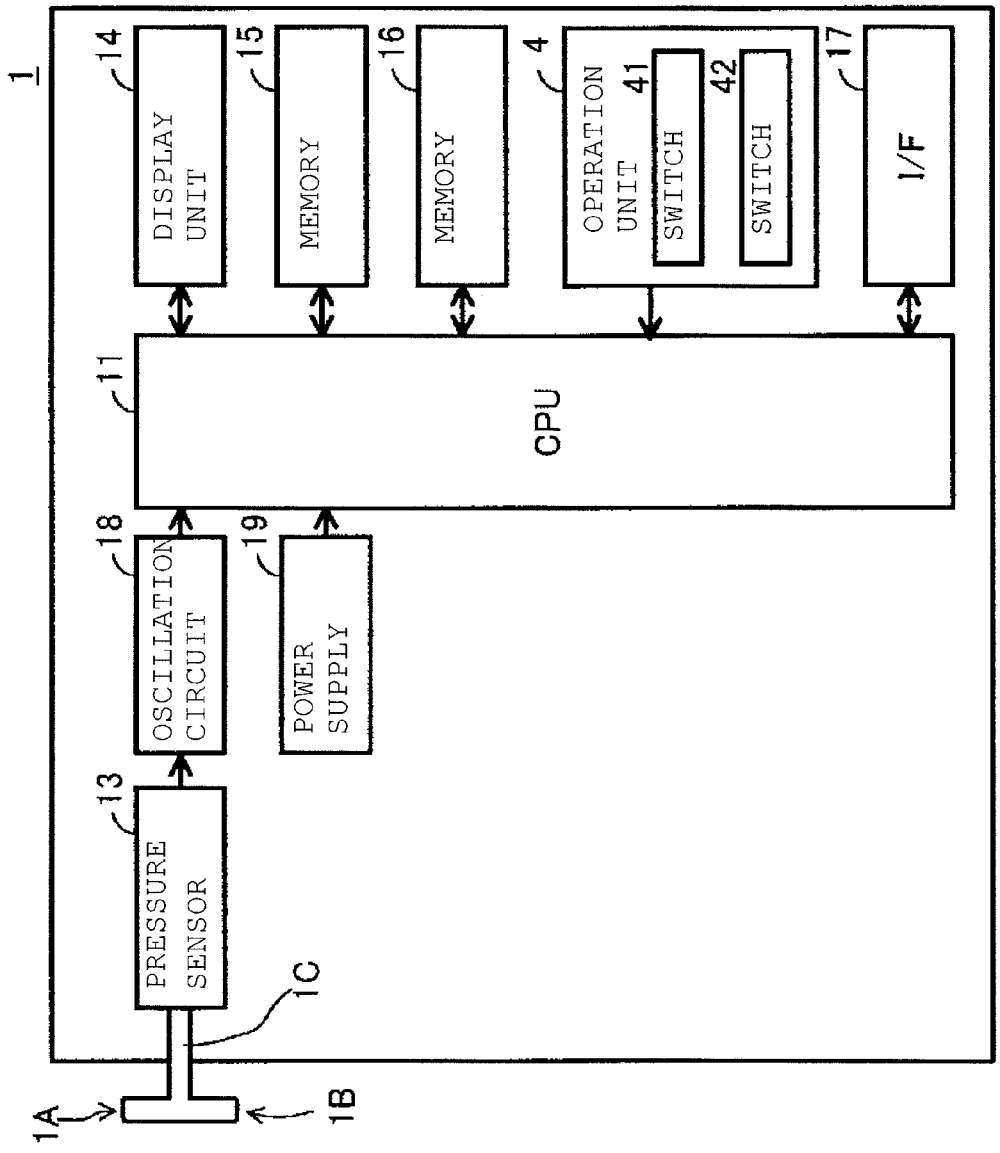
FIG. 2 is a block diagram showing a specific example of the hardware configuration of the module according to one or more embodiments of the present invention.

Referring to FIG. 2, the connection portions 1A and 1B are provided on an air passage 1C, and a pressure sensor 13 is further connected to the air passage 1C. The pressure sensor 13 is further connected to an oscillation circuit 18, and the oscillation circuit 18 is connected to a CPU (Central Processing Unit) 11. As the connection portion 1A is connected to the blood pressure meter 2 with the air tube 10A interposed therebetween, and the connection portion 1B is connected to the air bag 51 (see FIG. 4) included in the cuff 5 with the air tube 10B interposed therebetween, a closed space is constituted by the air tube 10A, the blood pressure meter 2, the air tube 10B, and the air bag 51.

Moreover, the display unit 14, memories 15 and 16, an interface (hereinafter, abbreviated to an I/F) 17, a power supply 19, and the operation unit 4 are connected to the CPU 11. The memory 15 is used for storing control programs or computation programs executed by the CPU 11, values used for control and computation, and the like. In addition, the memory 15 is also used as a work area when the CPU 11 executes the programs. The memory 16 is used for storing measurement results, computation results, and the like. The I/F 17 is an interface which is, in a case where the module 1 communicates with other apparatuses such as a personal computer or a recording medium writing apparatus, connected to the apparatuses via a communication cable for communication.

As the control programs, a program for causing the module 1 to perform a blood pressure measurement operation, a program for managing the measurement results stored in the memory 16, a program for displaying designated values, and the like are stored. The computation program corresponds to, for example, a program for computing and outputting an average value of the measurement results stored in the memory 16, a program for comparing the measurement results stored in the memory 16 to thresholds stored in advance and outputting the comparison results, or a program for comparing and analyzing the measurement results stored in the memory 16 according to the time and date.

The pressure sensor 13 is an electrostatic capacitive pressure sensor, and the capacitance value thereof is changed by a change in the internal pressure in the air passage 1C. The oscillation circuit 18 inputs a sensor signal at an oscillation frequency corresponding to the capacitance value of the pressure sensor 13 to the CPU 11. As the connection portion 1A is connected to the blood pressure meter 2 with the air tube 10A interposed therebetween, the connection portion 1B is connected to the air bag 51 (see FIG. 4) included in the cuff 5 with the air tube 10B interposed therebetween. The pressure sensor 13 detects the change in the internal pressure in the closed space constituted thereby.

The CPU 11 is driven by being supplied with power from the power supply 19. The CPU 11 executes a predetermined program stored in the memory 15 on the basis of an operation signal input from the operation unit 4. In a case where the executed program is a program for performing measurement, the CPU 11 determines the internal pressure of the air bag 51 on the basis of the sensor signal from the pressure sensor 13 using a coefficient stored in advance. The CPU 11 calculates a blood pressure value on the basis of the change in the internal pressure of the air bag 51, performs a process for displaying the measurement result on the display unit 14, and outputs data to be displayed and a control signal to the display unit 14. In a case where the executed program is a program for performing a computation corresponding to an operation signal input from the operation unit 4, the CPU 11 reads a designated measurement value from a predetermined area of the memory 16, performs the computation according to the program, performs a process for displaying the computation result on the display unit 14, and outputs data to be displayed and a control signal to the display unit 14.

Figure 3:
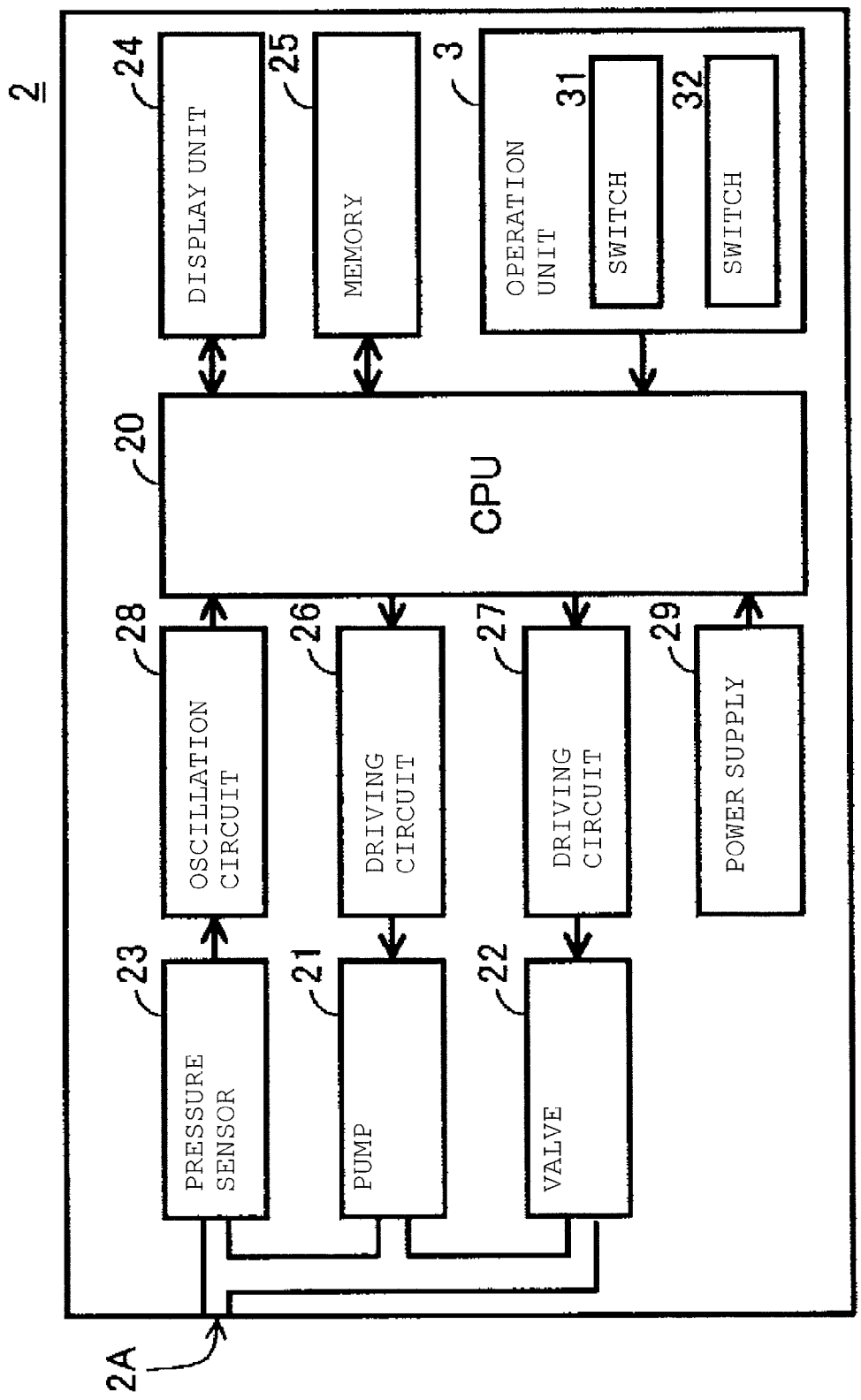
FIG. 3 is a block diagram showing a specific example of the hardware configuration of an existing electronic blood pressure meter.

Referring to FIG. 3, the blood pressure meter 2 includes a pressure sensor 23, a pump 21, and a valve 22, which are connected to the module 1 with the air tube 10A interposed therebetween. The pressure sensor 23, the pump 21, and the valve 22 are respectively connected to an oscillation circuit 28, a driving circuit 26, and a driving circuit 27, and moreover, the oscillation circuit 28, the driving circuit 26, and the driving circuit 27 are all connected to a CPU 20 for controlling the entire blood pressure meter 2.

Moreover, a display unit 24, a memory 25, and an operation unit 3 are connected to the CPU 20. The memory 25 is used for storing control programs executed by the CPU 20. In addition, the memory 25 is also used as a work area when the CPU 20 executes the programs. As the control program, a program for measurement for performing a typical blood pressure measurement operation is stored.

The CPU 20 executes the control program stored in the memory 25 on the basis of an operation signal input from the operation unit 3, and outputs control signals to the driving circuit 26 and the driving circuit 27. The driving circuit 26 and the driving circuit 27, respectively, drive the pump 21 and the valve 22 according to the control signals. Driving of the pump 21 is controlled by the driving circuit 26 according to the control signal from the CPU 20 to discharge air from the connection portion 2A. Opening and closing of the valve 22 is controlled by the driving circuit 27 according to the control signal from the CPU 20. In the case where the air tube 10A is connected to the connection portion 2A, and thus, the blood pressure meter 2 is further connected to the closed space with the air tube 10A interposed therebetween, air is injected into the closed space as the pump 21 is driven. The air in the closed space is discharged as the valve 22 is opened.

The pressure sensor 23 is an electrostatic capacitive pressure sensor, and the capacitance value thereof is changed by a change in the internal pressure in the closed space. The oscillation circuit 28 inputs a sensor signal at an oscillation frequency corresponding to the capacitance value of the pressure sensor 23 to the CPU 20.

The CPU 20 is driven by being supplied with power from a power supply 29. The CPU 20 determines the internal pressure of the air bag 51 on the basis of the sensor signal from the pressure sensor 23 using a coefficient stored in advance. The CPU 20 calculates a blood pressure value on the basis of the change in the internal pressure of the air bag 51, performs a process for displaying the measurement result on the display unit 24, and outputs data to be displayed and a control signal to the display unit 24.

Figure 4:
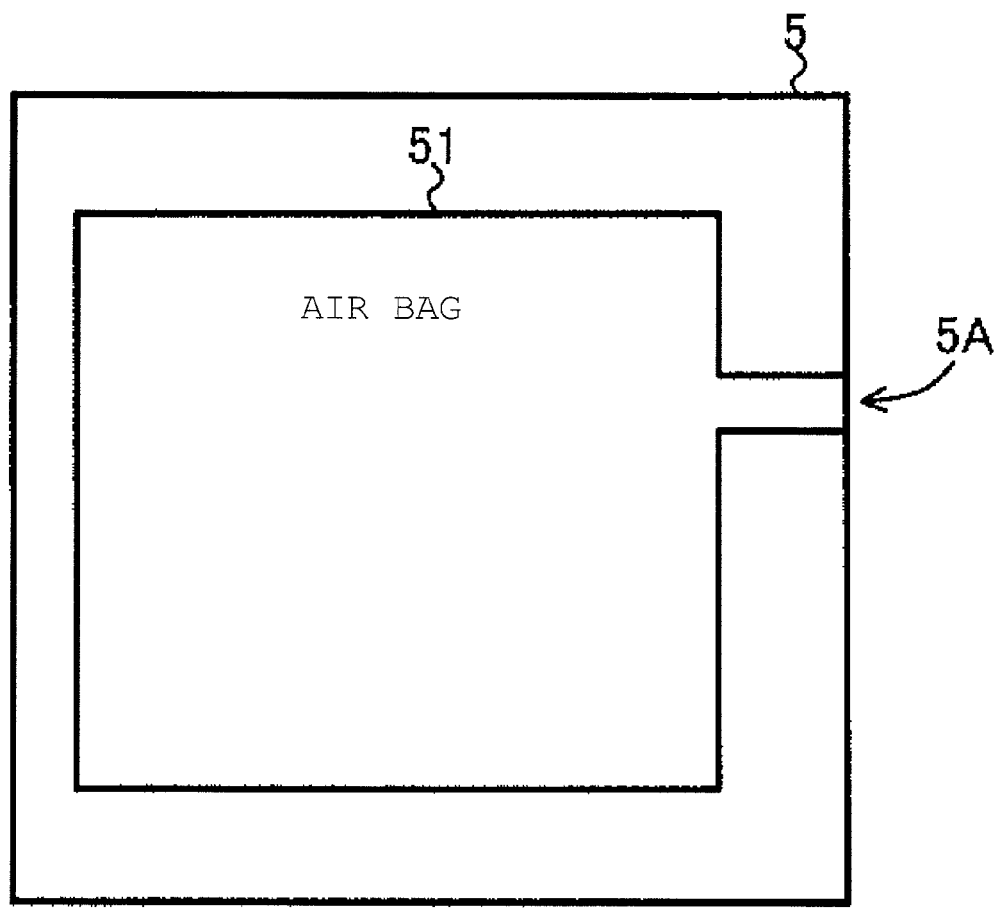
FIG. 4 is a block diagram showing a specific example of the configuration of a cuff.

Referring to FIG. 4, the cuff 5 includes the air bag 51 therein.

Figure 5:
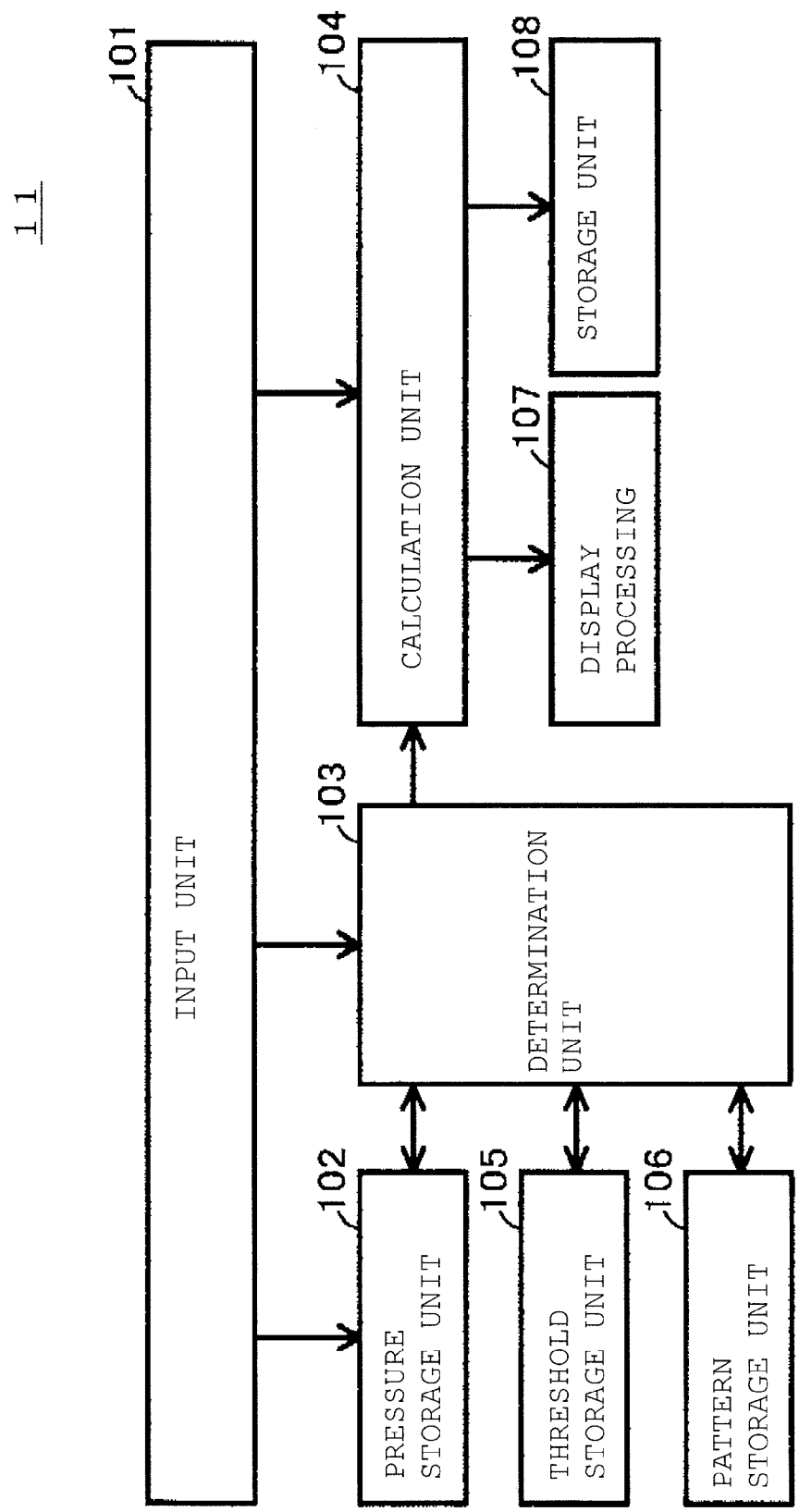
FIG. 5 is a block diagram showing a function for performing a measurement operation by the module according to one or more embodiments of the present invention.

Referring to FIG. 5, the module 1 includes, as functions for performing a measurement operation, an input unit 101, a pressure storage unit 102, a determination unit 103, a calculation unit 104, a threshold storage unit 105, a pattern storage unit 106, a display processing unit 107, and a storage unit 108. The functions are executed as the CPU 11 reads out the control program stored in the memory 15 in response to the operation signal from the operation unit 4 and are mainly formed in the CPU 11. However, at least a part of the functions may also be formed to include any of the hardware configurations shown in FIG. 2.

The input unit 101 receives an input of the sensor signal from the pressure sensor 13 and inputs a value represented by the sensor signal to the pressure storage unit 102, the determination unit 103, and the calculation unit 104. The pressure storage unit 102 is configured as a storage device included in the CPU 11, the memory 15, or a partial area of the memory 16, and temporarily stores the value input from the input unit 101. The determination unit 103 determines whether or not to perform a blood pressure calculation using the value input from the input unit 101 and a value stored in the pressure storage unit 102, and using the value input from the input unit 101. At this time, the determination may be performed using a threshold, which is described later, stored in advance in the threshold storage unit 105 and/or a pattern, which is described later, stored in advance in the pattern storage unit 106. The calculation unit 104 calculates blood pressure from the value input from the input unit 101 according to the determination of the determination unit 103 and inputs the calculated blood pressure to the display processing unit 107 and the storage unit 108. The display processing unit 107 generates data to display the calculated blood pressure on the display unit 14 as a measurement result and outputs a control signal to the display unit 14. The storage unit 108 performs a process for storing the calculated blood pressure in a predetermined area of the memory 16 as the measurement result.

Figure 6A:
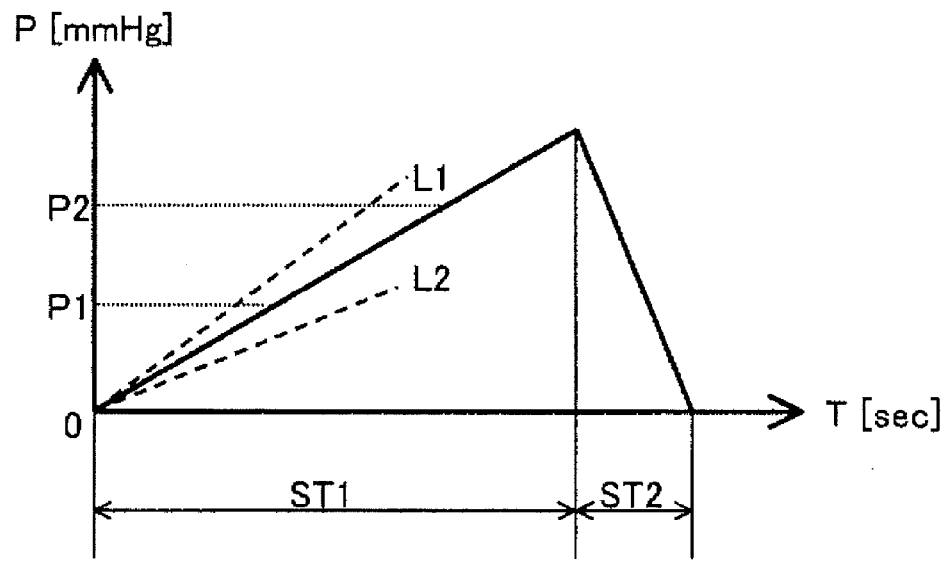
FIG. 6A is a diagram showing a specific example of a change in cuff pressure during blood pressure measurement by an electronic blood pressure meter of a pressurization measurement type.
Figure 6B:
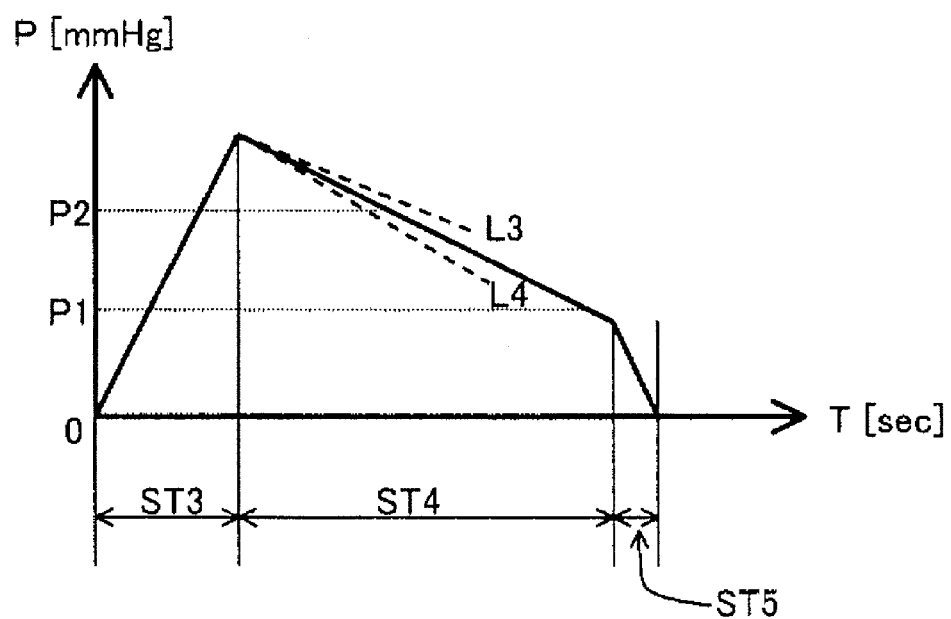
FIG. 6B is a diagram showing a specific example of a change in cuff pressure during blood pressure measurement by an electronic blood pressure meter of a depressurization measurement type.

When blood pressure is measured by the blood pressure meter 2, the pump 21 injects air into the air bag 51 according to the control of the CPU 20 and pressurizes the air bag 51 until the internal pressure of the air bag 51 becomes a predetermined pressure. The predetermined pressure is a pressure higher than the highest blood pressure. When the internal pressure reaches the predetermined pressure, the valve 22 is opened, and the air in the air bag 51 is discharged, so that the internal pressure of the air bag 51 is depressurized. When blood pressure is measured by an electronic blood pressure meter on the basis of a change in internal pressure of an air bag, there is a method of calculating a blood pressure value on the basis of the change in the internal pressure during the above-mentioned pressurization process and a method of calculating a blood pressure value on the basis of the change in the internal pressure during the above-mentioned depressurization process. A case of employing the former method is called a pressurization measurement type, and a case of employing the latter method is called a depressurization measurement type. In the case where the blood pressure meter 2 is of the pressurization measurement type, the change in the internal pressure of the air bag 51 is gradually pressurized in a period of ST1 and is rapidly depressurized in a period of ST2 as shown in FIG. 6A. In the case where the blood pressure meter 2 is of the depressurization measurement type, the change in the internal pressure of the air bag 51 is rapidly pressurized in a period of ST3 and is gradually depressurized in a period of ST4 as shown in FIG. 6B. In a period of ST5 after the lowest blood pressure is calculated, rapid depressurization is made. This is for enhancing measurement precision by gradually changing the internal pressure of the air bag 51 in a period in which a sensor value for the blood pressure value calculation is obtained. In the pressurization measurement type, according to one or more embodiments of the present invention, a pressurization speed is in a predetermined range in which a prescribed measurement precision is obtained. Similarly, in the depressurization measurement type, according to one or more embodiments of the present invention, a depressurization speed is in a predetermined range in which a prescribed measurement precision is obtained. In FIG. 6A, the slope of the predetermined range corresponding to a change in the pressure during pressurization is shown between the slope of a straight line L2 and the slope of a straight line L1. In FIG. 6B, the slope of the predetermined range corresponding to a change in the pressure during depressurization is shown between the slope of a straight line L4 and the slope of a straight line L3.

The module 1 calculates a blood pressure value on the basis of a sensor signal in the period ST1, which is a pressurization period in the case where the blood pressure meter 2 is of the pressurization measurement type. In the case where the blood pressure meter 2 is of the depressurization measurement type, the blood pressure value is calculated on the basis of a sensor signal in the period ST4, which is a depressurization period. There, the determination unit 103 determines whether it is the pressurization period or the depressurization period, from a value input from the input unit 101 and a value input from the input unit 101 immediately therebefore and stored in the pressure storage unit 102.

According to one or more embodiments of the present invention, in the case where the blood pressure meter 2 is of the pressurization measurement type, in the period ST1, which is the pressurization period, and in the case where the pressurization speed is between the inclination of the straight line L2 and the inclination of the straight line L1, the module 1 calculates a blood pressure value on the basis of the sensor signal in the period. Similarly, in the case where the blood pressure meter 2 is of the depressurization measurement type, in the period ST4, which is the depressurization period, and in the case where the depressurization speed is between the inclination of the straight line L4 and the slope of the straight line L3, the module 1 calculates a blood pressure value on the basis of the sensor signal. There, the threshold storage unit 105 stores the slopes of the straight lines L1 and L2 as thresholds for determining whether or not it is in a suitable pressurization period for blood pressure measurement and stores the slopes of the straight lines L3 and L4 as thresholds for determining whether or not it is in an appropriate depressurization period for blood pressure measurement. The determination unit 103 determines whether it is a suitable pressurization period for blood pressure measurement or a suitable depressurization period for blood pressure measurement from the value input from the input unit 101 and the value input from the input unit 101 immediately therebefore and stored in the pressure storage unit 102.

Figure 7:
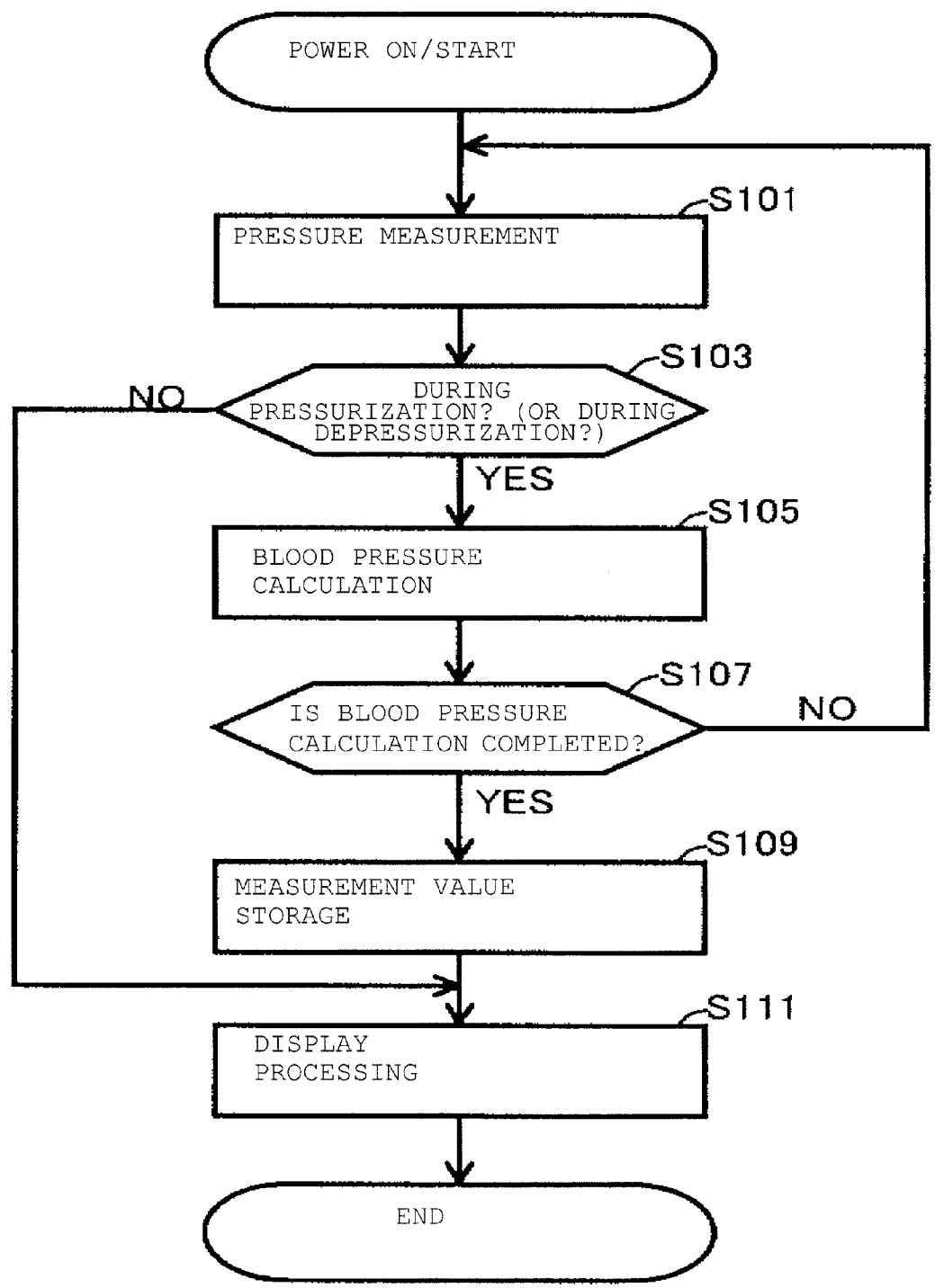
FIG. 7 is a flowchart showing a specific flow of operations in the module according to the embodiment.

Using FIG. 7, as a specific flow of operations performed in the module 1, a flow of operations performed in the case where the blood pressure meter 2 is of the pressurization measurement type will be described. The CPU 11 reads and executes the control program stored in the memory 15 according to the operation signal from the operation unit 4 to exhibit each of the functions shown in FIG. 5, thereby realizing a series of operations. The operations of the module 1 shown in FIG. 7 are started when the switch 41 is pressed down and power is supplied to the CPU 11 from the power supply 19. Otherwise, even in the power off state, in a low power state in which a low level of power is supplied from the power supply 19, and in a case where in the low power state the CPU 11 detects a predetermined amount (for example, of equal to or greater than a threshold stored in advance) of the change in the internal pressure in the air passage 1C from the pressure sensor 13, powering on is determined, and the operations may be controlled to supply startup power to the power supply 19. In addition, the operations of the module 1 shown in FIG. 7 may be started when the startup power is supplied.

Referring to FIG. 7, in Step S101, a pressure in the air bag 51, which is the closed space connected with the interposed air tubes 10A and 10B, is measured by the pressure sensor 13, and a sensor signal is input to the input unit 101. The determination unit 103 determines whether or not a current time point is during pressurization, that is, in the period ST1 of FIG. 6A, by comparing the value represented by the sensor signal input in Step S101 to the value stored in the pressure storage unit 102 and measured immediately therebefore. Here, according to one or more embodiments of the present invention, the determination unit 103 determines whether or not it is during pressurization, and if during pressurization, whether the pressurization speed is a suitable pressurization speed for blood pressure measurement, which is between the slope of the straight line L2 and the slope of the straight line L1. Moreover, the determination unit 103 compares the thresholds, which are the slopes of the straight lines L1 and L2 stored in the threshold storage unit 105, to a slope obtained from the value represented by the sensor signal input in Step S101 and the value stored in the pressure storage unit 102 and measured immediately therebefore. Therefore, in the case where the blood pressure meter 2 is of the pressurization measurement type, in Step S103 of FIG. 7, the following operations diverge according to the determination result of whether or not it is during pressurization.

If the determination unit 103 determines that the time point measured in Step S101 is during pressurization, or determines that the time point is during the pressurization in which the pressurization speed is a suitable pressurization speed for blood pressure measurement (YES in Step S103), the calculation unit 104 in Step S105 calculates a blood pressure value from the value measured in Step S101.

The operations of Steps S101 to S105 are repeated until the blood pressure calculation is completed by the calculation in Step S105, that is, until the highest blood pressure and the lowest blood pressure are calculated. Until the blood pressure calculation is completed by the calculation in Step S105, that is, when the highest blood pressure and the lowest blood pressure are calculated (YES in Step S107), the storage unit 108 in Step S109 performs a process for storing values representing the highest blood pressure and the lowest blood pressure obtained in Step S105 in a predetermined area of the memory 16 as a measurement result and stores the measurement results. Moreover, the display processing unit 107 in Step S111 generates data for displaying the values representing the highest blood pressure and the lowest blood pressure obtained in Step S105 on the display unit 14 as the measurement result and displays the data on the display unit 14. In Step S111, by changing (or in addition to) the display, a process of outputting the measurement result to another apparatus (for example, a personal computer or the like) connected from the I/F 17 may be performed. This is the same in the following description. Thereafter, the CPU 11 ends the series of operations.

In a case where the time point measured in Step S101 is not during pressurization or, in a case where, even during pressurization, the pressurization speed is not a suitable pressurization speed for blood pressure measurement (NO in Step S103), the CPU 11 may end the series of operations as they are, or as shown in FIG. 7, the series of operations may be ended after the display processing unit 107 performs an error display on the display unit 14 using data for display stored in advance in Step S111.

Even in the case where the blood pressure meter 2 is of the depressurization measurement type, the module 1 performs the operations shown in FIG. 7. That is, in this case, the determination unit 103 determines whether or not a current time point is during depressurization, that is, in the period ST4 of FIG. 6B by comparing the value represented by the sensor signal input in Step S101 to the value stored in the pressure storage unit 102 and measured immediately therebefore. Here, according to one or more embodiments of the present invention, the determination unit 103 determines whether or not it is during depressurization, and if during depressurization, whether the depressurization speed is a suitable depressurization speed for blood pressure measurement, which is between the slope of the straight line L4 and the slope of the straight line L3, by further comparing the thresholds, which are the slopes of the straight lines L3 and L4 stored in the threshold storage unit 105, to a slope obtained from the value represented by the sensor signal input in Step S101 and the value stored in the pressure storage unit 102 and measured immediately therebefore. Therefore, in the case where the blood pressure meter 2 is of the depressurization measurement type, in Step S103 of FIG. 7, the following operations diverge according to the determination result of whether or not it is during depressurization. If the determination unit 103 determines that the time point measured in Step S101 is during depressurization, or determines that the time point is during the depressurization in which the depressurization speed is a suitable depressurization speed for blood pressure measurement (YES in Step S103), a blood pressure value is calculated as described above and an operation of storing and displaying the calculated blood pressure value is performed.

As the module 1 performs the above-described operations, situations in which a suitable value is not calculated because blood pressure is calculated from a sensor signal in a period in which the measurement operation is not performed by the blood pressure meter 2, blood pressure is calculated after the measurement by the blood pressure meter 2 is stopped, blood pressure is calculated from a sensor signal in the pressurization period (the period ST3 of FIG. 6B) in a case where the module 1 of the pressurization measurement type is connected to the blood pressure meter of the depressurization measurement type by mistake, or blood pressure is calculated from a sensor signal during the depressurization period (the period ST2 of FIG. 6A) in a case where the module 1 of the depressurization measurement type is connected to the blood pressure meter of the pressurization measurement type by mistake, can be automatically prevented, thereby measuring blood pressure with good precision.

Moreover, as the module 1 performs the above-described operations, when blood pressure is measured by the blood pressure meter 2, similarly, the blood pressure is also measured by the module 1, and the measurement result is stored in the predetermined area of the memory 16. Therefore, even in a case where the blood pressure meter 2 is not provided with a memory function, the measurement result may be stored in the module 1. Moreover, the memory 15 of the module 1 stores the above-mentioned computation programs. Therefore, even in a case where the blood pressure meter 2 is not provided with a computation function, the module 1 can perform various computations using the measurement results stored in the memory 16. That is, even when the blood pressure meter 2 has low functionality, by connecting the module 1 to the blood pressure meter 2 and the cuff 5 with the air tubes 10A and 10B, the function provided in the module 1 can be used for the measurement results. Therefore, without changing the blood pressure meter 2 and providing a new blood pressure meter having high functionality, which has the function provided in the module 1, by providing the module 1, a blood pressure module having such functions can be realized. As shown in FIGS. 2 and 3, the module 1 does not include a mechanism for internal pressure control for a blood pressure meter, and thus is small and light-weight compared to the blood pressure meter 2 and is easy to handle by a user. In addition, because the mechanism is not included therein, high functionality is obtained with lower costs than providing a new blood pressure meter.

Modified Example 1

In the above example, the module 1 performs a different operation depending on which of the pressurization measurement type and the depressurization measurement type is employed by the blood pressure meter 2. Therefore, the module 1 needs to be connected to a suitable blood pressure meter 2 in advance for the measurement methods or to designate the measurement method of the blood pressure meter 2 by providing a switch (not shown). In the latter case, when the operations of FIG. 7 are started, first, designation of the measurement method of the blood pressure meter 2 is received, and by reading a control program corresponding to this, the operations diverge to the operations for the pressurization measurement type (FIG. 7) or operations for the depressurization measurement type.

According to one or more embodiments of the present invention, using FIG. 8 as a first modified example of the operations of the module 1, an example in which a measurement method is employed by the blood pressure meter 2 as determined from a measured pressure and the operations automatically diverse will be described. The operations of FIG. 8 are also realized as the CPU 11 reads and executes the control program stored in the memory 15 according to the operation signal from the operation unit 4 to exhibit each of the functions shown in FIG. 5.

Figure 8:
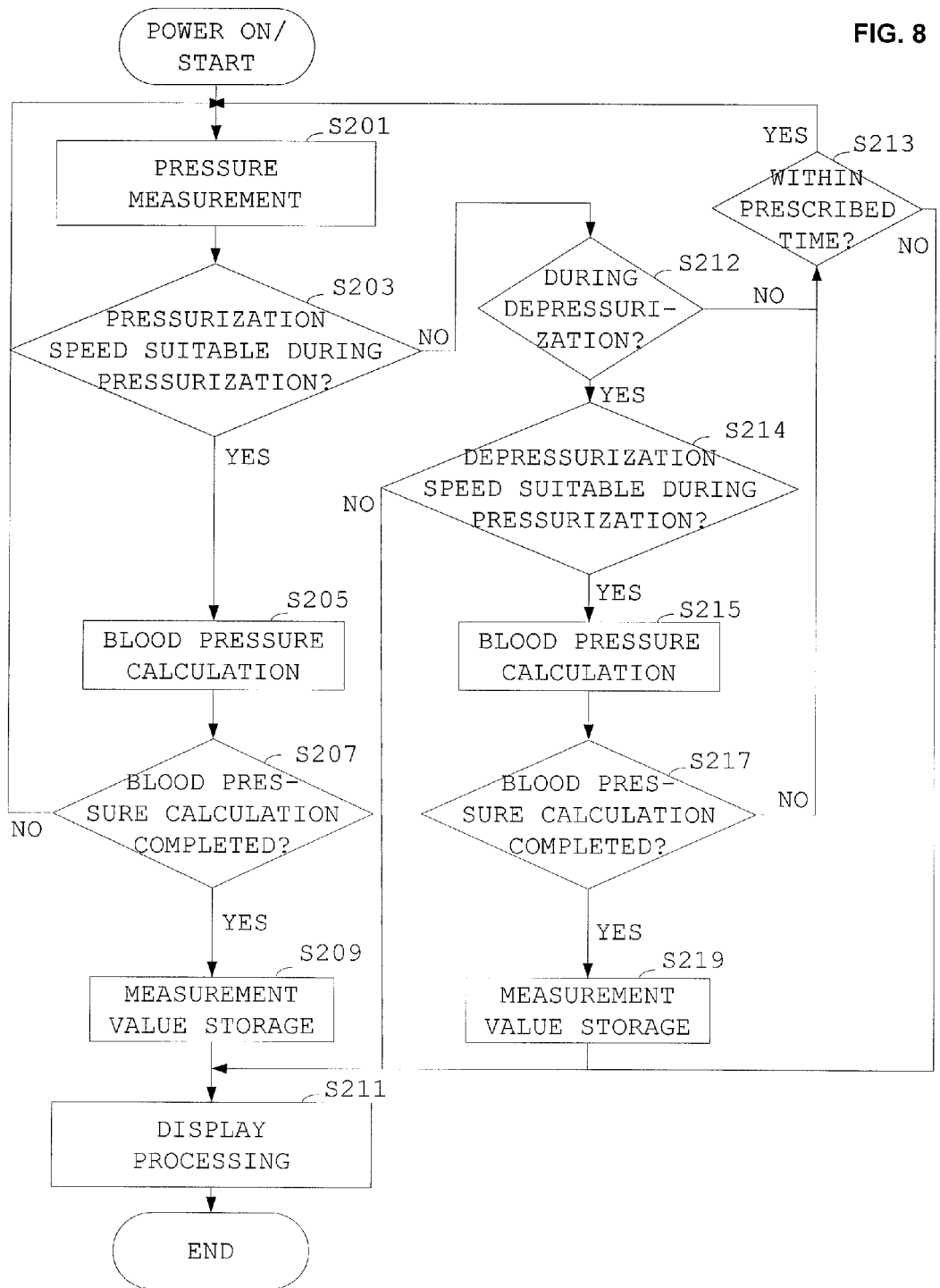
FIG. 8 is a flowchart showing a first modified example of the operations in the module according to the embodiment.

Referring to FIG. 8, in Step S201, pressure in the air bag 51, which is the closed space connected with the interposed air tubes 10A and 10B, is measured by the pressure sensor 13, and a sensor signal is input to the input unit 101. The determination unit 103 determines whether or not a current time point is during pressurization in the pressurization measurement type by comparing the value represented by the sensor signal input in Step S201 to the value stored in the pressure storage unit 102 and measured immediately therebefore. Specifically, the determination unit 103 determines whether or not it is during pressurization from the value represented by the sensor signal input in Step S201 and the value stored in the pressure storage unit 102 and measured immediately therebefore, and moreover, by comparing the thresholds which are the slopes of the straight lines L1 and L2 stored in the threshold storage unit 105 to a slope obtained from the value represented by the sensor signal input in Step S201 and the value stored in the pressure storage unit 102 and measured immediately therebefore. The determination unit 103 determines whether or not it is during pressurization in which the pressurization speed is a suitable pressurization speed for blood pressure measurement, which is between the slope of the straight line L2 and the slope of the straight line L1. That is, even during pressurization, the pressurization period of the pressurization measurement type (the period ST1 of FIG. 6A) other than the pressurization period (the period ST3 of FIG. 6B) of the depressurization measurement type is determined by the determination unit 103. If determination is made as such (YES in Step S203), in Step S205, the calculation unit 104 calculates a blood pressure value from the measurement value in Step S201, and the operations are repeated until the highest blood pressure and the lowest blood pressure are calculated by the calculation unit 104. Thereafter, like the operations of FIG. 7, the measurement result is stored and displayed (Steps S209 and S211).

On the other hand, if it is determined that the time point measured in Step S201 is not in the pressurization period of the pressurization measurement type shown by the period ST1 of FIG. 6A (NO in Step S203), the determination unit 103 determines whether or not it is during depressurization from the value represented by the sensor signal input in Step S201 and the value stored in the pressure storage unit 102 and measured immediately therebefore. If it is determined that the time point is not during the depressurization, that is, the time point is in the pressurization period that is not the pressurization period of the pressurization measurement type (for example, the period ST3 of FIG. 6B) (NO in Step S212), the determination unit 103 repeats the determination based on the input value until the time point is during depressurization. In addition, the CPU 11 repeatedly performs this operation for a prescribed time (for example, a time needed for a single blood pressure measurement operation or the like), and at a time point after the time elapses (YES in Step S213), the operation is compulsively ended.

If it is determined that the time point measured in Step S201 is during depressurization (YES in Step S212), the determination unit 103 determines whether or not the depressurization speed is a suitable depressurization speed for blood pressure measurement, which is between the slope of the straight line L4 and the slope of the straight line L3. Moreover, the determination unit 103 compares the thresholds, which are the slopes of the straight lines L3 and L4 stored in the threshold storage unit 105 to a slope obtained from the value represented by the sensor signal input in Step 5201 and the value stored in the pressure storage unit 102 and measured immediately therebefore. If determination is made as such (YES in Step S214), in Step S215, the calculation unit 104 calculates a blood pressure value from the measurement value in Step S201, and the operations are repeated until the highest blood pressure and the lowest blood pressure are calculated by the calculation unit 104. Thereafter, like the operations of FIG. 7, the measurement result is stored and displayed (Steps S219 and S211).

Even when the time point measured in Step S201 is during pressurization, if a prescribed time elapses without a transition to depressurization during pressurization in which the pressurization speed is not suitable for blood pressure measurement in the pressurization measurement type (NO in Step S203, NO in S212, and NO in S213), or even when the time point is during depressurization, if the depressurization speed is not suitable for blood pressure measurement in the depressurization measurement type (NO in Step S203, YES in Step S212, and NO in Step S214), the CPU 11 may end the series of operations as they are, or as shown in FIG. 8, may end the series of operations after the display processing unit 107 performs an error display on the display unit 14 in Step S211 using data for display stored in advance.

As the module 1 performs the operations according to the first modified example described above, when the blood pressure meter 2 is of either of the pressurization measurement type and the depressurization measurement type, the type is automatically determined, and suitable operations therefor are performed to measure blood pressure. Therefore, the user does not need to distinguish the module 1 between the measurement methods of the blood pressure meter 2 for use. In addition, the user does not need to perform an operation for determining and instructing which measurement method is employed by the blood pressure meter 2. Moreover, by the above determination, situations in which a suitable value is not calculated because blood pressure is calculated from a sensor signal in the pressurization period (the period ST3 of FIG. 6B) of the depressurization measurement type, blood pressure is calculated from a sensor signal during the depressurization period (the period ST2 of FIG. 6A) of the pressurization measurement type or in the period (the period ST5 of FIG. 6B) in which rapid depressurization is made in the depressurization measurement type, or blood pressure is calculated after measurement by the blood pressure meter 2 is stopped, can be automatically prevented, thereby measuring blood pressure with good precision.

Modified Example 2

A method of measuring blood pressures of a plurality of persons to be measured using the blood pressure meter 2 and storing the measurement result of each of the measured persons has been considered. In a case where the blood pressure meter 2 does not have a memory function, the function may be realized by the module 1.

In a case where the memory 16 of the module 1 has a storage area for a single person to be measured, by connecting the module 1 corresponding to the person to be measured between the blood pressure meter 2 and the cuff 5 as shown in FIG. 1, the measurement result for the measured person corresponding to the memory 16 may be stored. That is, the module 1 is reconnected for each person to be measured so as to store the measurement result for the corresponding person to be measured.

Figure 9:
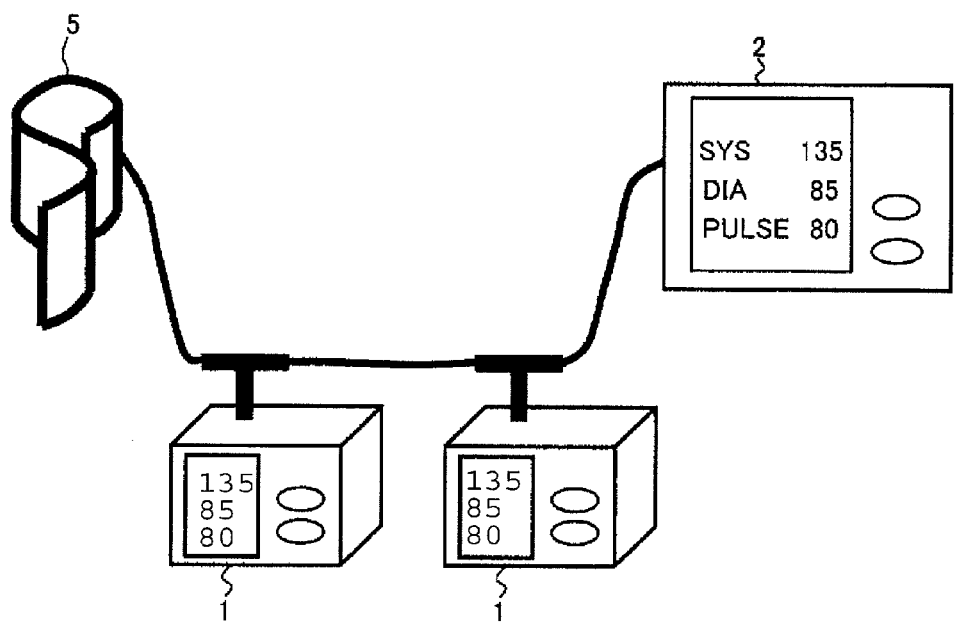
FIG. 9 is a diagram showing a specific example of the configuration of a module according to a second modified example.

As another method, as shown in FIG. 9, a plurality of modules 1 corresponding to respective persons to be measured is connected between the blood pressure meter 2 and the cuff 5, and measurement is performed by the corresponding module 1, thereby storing the measurement result of the measured person corresponding to the module 1.

Figure 10:
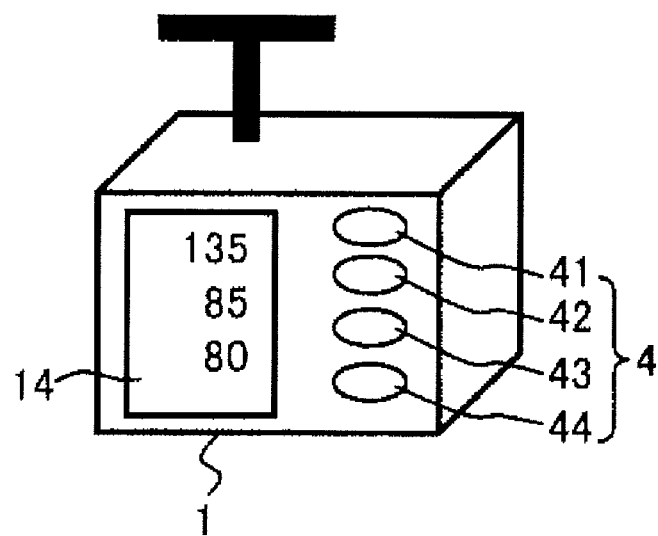
FIG. 10 is a diagram showing a specific example of the outer appearance of the module according to the second modified example.

Otherwise, in a case where the memory 16 of the module 1 includes storage areas corresponding to a plurality of persons to be measured, the measurement result may be stored in the storage area corresponding to the designated person to be measured. In this case, according to one or more embodiments of the present invention, the operation unit 4 of the module 1 includes switches 43 and 44 for designating persons to be measured as shown in FIG. 10. The switches correspond to the persons to be measured and are included for the number of persons. The storage unit 108 stores the storage areas of the memory 16 corresponding to the switches 43 and 44 in advance. When the CPU 11 receives an operation signal for designating a person to be measured from the operation unit 4 at a predetermined time such as at the start of measurement, in Step S109, the storage unit 108 stores the measurement result in the storage area of the memory 16 corresponding to the operated switch.

As the module 1 is used as such, or performs the configuration and operation as shown in FIG. 9, the measurement result is stored so as to be associated with the measured person in the module 1. Therefore, even in the case where the blood pressure meter 2 does not have the operation function, the module 1 can perform various operations using the measurement result stored for each of the measured persons in the memory 16.

Modified Example 3

In the above example, when the blood pressure meter 2 is a general electronic blood pressure meter of a pressurization measurement type or a depressurization measurement type, a configuration in which any electronic blood pressure meter measures blood pressure using the module 1 providing various possible operations is shown. However, there are electronic blood pressure meters which perform pressurization or depressurization in a special method. In addition, the module 1 may be permitted to be used particularly for such a specific electronic blood pressure meter and may not be permitted to be used for other electronic blood pressure meters.

As a specific example of an electronic blood pressure meter that is of the pressurization measurement type and performs pressurization by the special method, for example, the applicant of the invention discloses a method of changing a pressurization speed using the fuzzy theory in JP-A-4-158833. In addition, in JP-A-10-314132, a method of changing a pressurization speed as a curve is disclosed. As a specific example of the electronic blood pressure meter that is of the depressurization measurement type and performs pressurization by the special method, for example, the applicant of the invention discloses a method of performing rapid depressurization to a band to be measured and performs gradual depressurization in the band in JP-A-6-38935 or JP-A-7-8464.

Figure 11A:
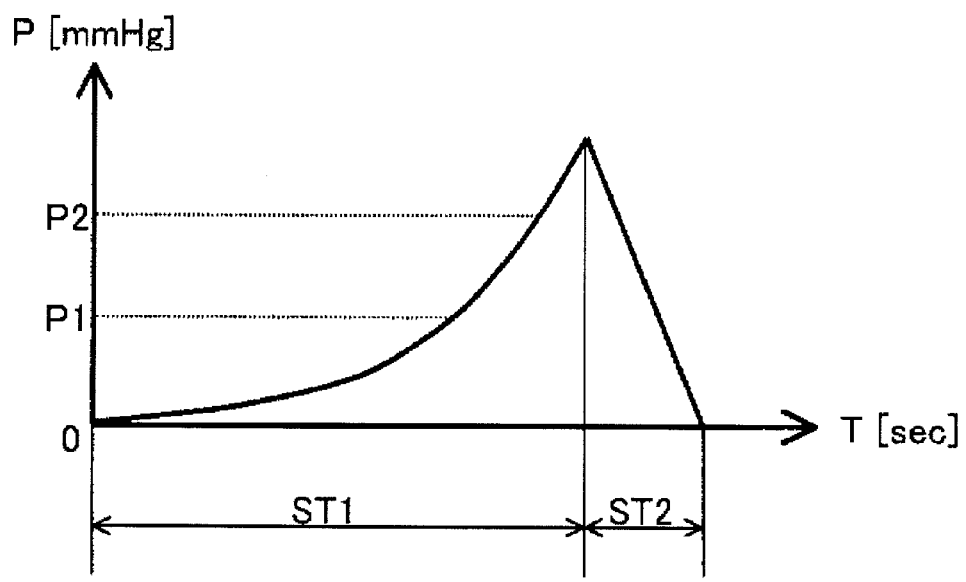
FIG. 11A is a diagram showing another specific example of the change in the cuff pressure during blood pressure measurement.
Figure 11B:
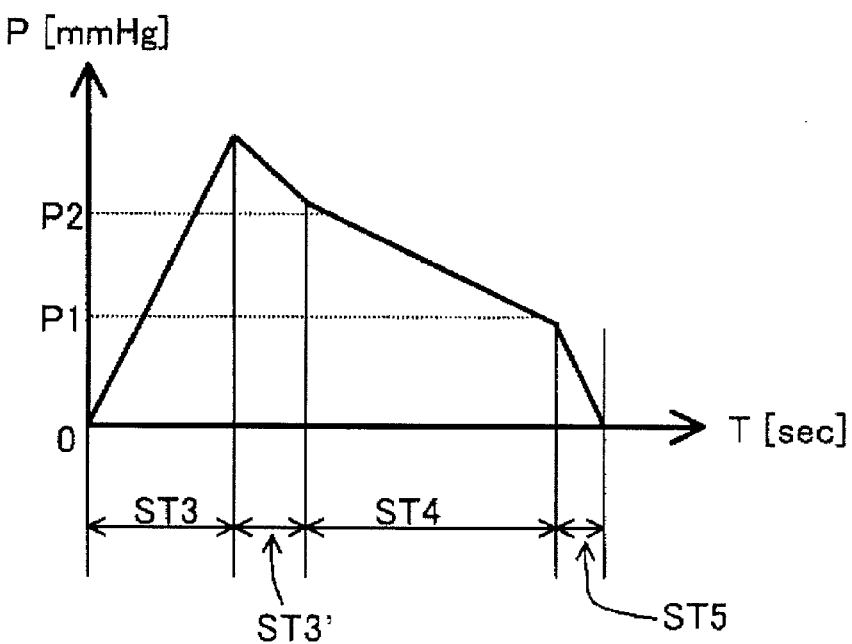
FIG. 11B is a diagram showing another specific example of the change in the cuff pressure during blood pressure measurement.

In the case where the blood pressure meter 2 is the electronic blood pressure meter that performs pressurization or depressurization by the special methods, the internal pressure of the air bag 51 is changed in a predetermined pattern. For example, in the case where the blood pressure meter 2 is an electronic blood pressure meter that measures blood pressure by changing a pressurization speed as a curve as disclosed in JP-A-10-314132, the internal pressure of the air bag 51 is changed as a curve in a period ST1 as shown in FIG. 11A. In addition, in the case where the blood pressure meter 2 is an electronic blood pressure meter that measures blood pressure by changing a depressurization speed in stages as disclosed in JP-A-6-38935 or JP-A-7-8464, the internal pressure of the air bag 51 is rapidly reduced in a period ST3' as shown in FIG. 11B. The module 1 according to the third modified example stores a predetermined pattern of the change in the internal pressure, for example, as shown in FIG. 11A or 11B, in the pattern storage unit 106. The determination unit 103 compares the change in the internal pressure of the air bag 51 obtained from the value input from the input unit 101 and the value input from the input unit 101 immediately therebefore and stored in the pressure storage unit 102 to the pattern stored in the pattern storage unit 106, thereby determining whether or not they correspond with each other or substantially correspond with each other. Specifically, for example, the determination unit 103 obtains a correlation between a straight line (or a curve) obtained from the value input from the input unit 101 and the value input from the input unit 101 immediately therebefore and stored in the pressure storage unit 102 and a straight line (or a curve), which is the pattern stored in the pattern storage unit 106, and in a case where the correlation is equal to or greater than a predetermined value prescribed in advance, determines that the correlation corresponds with the pattern; that is, the connected blood pressure meter 2 is a permitted electronic blood pressure meter.

Using FIG. 12, operations including authentication of the blood pressure meter 2 connected as the third modified example of the operations of the module 1 will be described. The operations of FIG. 12 are also realized as the CPU 11 reads and executes the control program stored in the memory 15 according to the operation signal from the operation unit 4 to exhibit each of the functions shown in FIG. 5.

Figure 12:
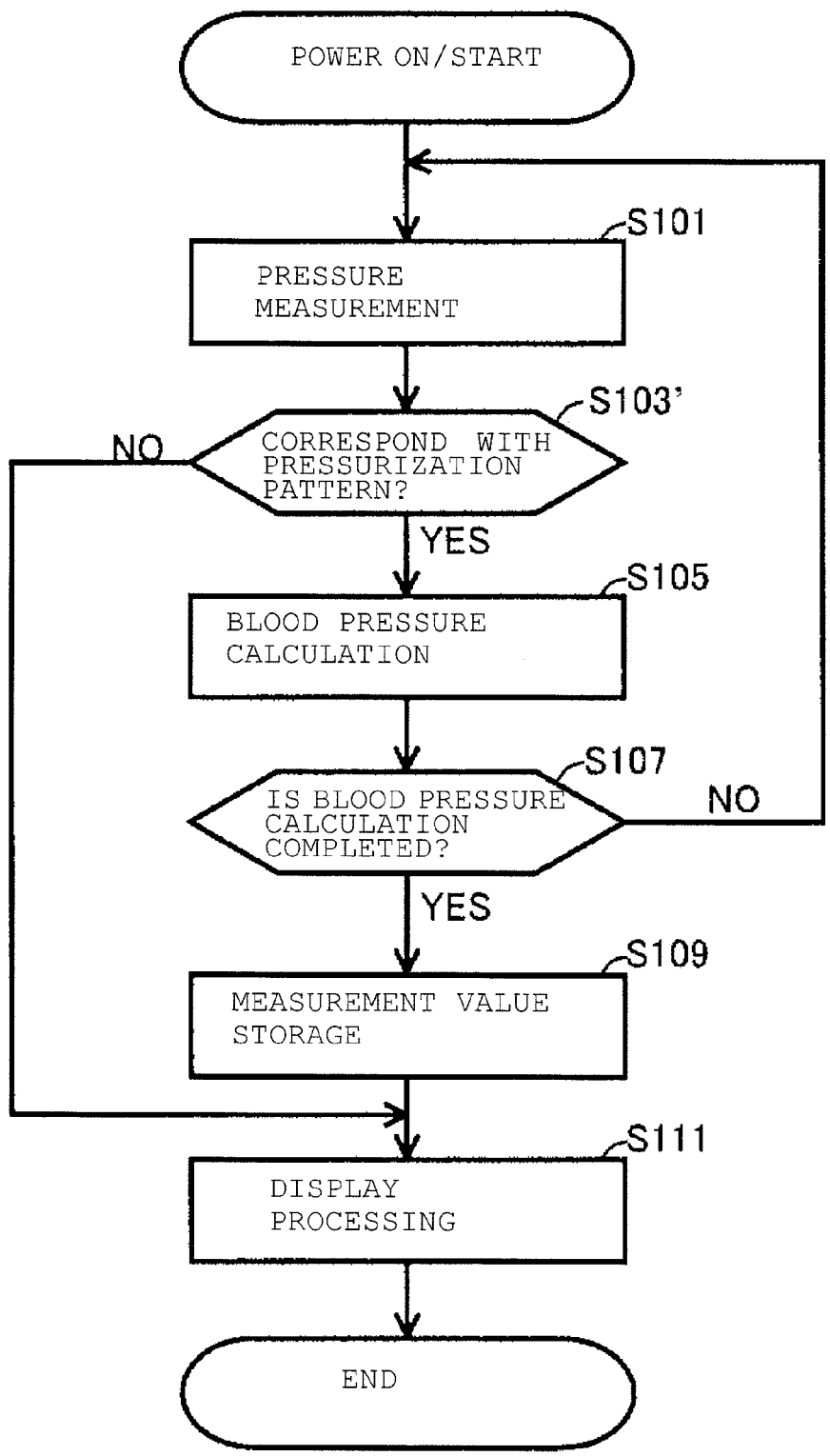
FIG. 12 is a flowchart showing a third modified example of the operations in the module according to one or more embodiments of the present invention.

Referring to FIG. 12, like FIG. 7, in Step S101, pressure in the air bag 51, which is the closed space connected with the interposed air tubes 10A and 10B, is measured by the pressure sensor 13, and a sensor signal is input to the input unit 101. The determination unit 103 compares the change in the internal pressure of the air bag 51 obtained from the value input from the input unit 101 and the value input from the input unit 101 immediately therebefore and stored in the pattern storage unit 102 to the pattern stored in the pattern storage unit 106, thereby determining whether or not they correspond with each other or substantially correspond with each other. In the determination unit 103 in the third specific example, the values stored in the pressure storage unit 102 may be more frequently used than during determination in the operations shown in FIG. 7 or FIG. 8.

In the determination unit 103, when it is determined that the change in the internal pressure of the air bag 51 obtained from the value input from the input unit 101 and the value input from the input unit 101 immediately therebefore and stored in the pressure storage unit 102 corresponds with or substantially corresponds with the pattern stored in the pattern storage unit 106 (YES in Step S103'), thereafter, the same operations as the operations from Step S105 of FIG. 7 are performed, and a blood pressure value is calculated by the calculation unit 104 and is then stored and displayed.

As another operation example, even in a case where any determination is made, a blood pressure value is calculated by the calculation unit 104, and when it is determined that the calculated blood pressure value corresponds with or substantially corresponds with the pattern, a process for displaying the measurement result may be performed by the display processing unit 107.

As the module 1 stores the pattern as shown in FIG. 11 and performs the operations according to the above-described third modified example, in a case where the permitted electronic blood pressure meter on which the pattern is registered in advance is connected as the blood pressure meter 2, the measurement result is stored. In this manner, a method may be applied where only electronic blood pressure meters with high reliability are permitted, so that a measurement result with high reliability can be obtained.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

DESCRIPTION OF REFERENCE NUMERALS

1: MODULE
1A, 1B, 2A, 5A: CONNECTION PORTION
1C: AIR PASSAGE
2: BLOOD PRESSURE METER
3,4: OPERATION UNIT
5: CUFF
10, 10A, AND 10B: AIR TUBE
11, 20: CPU
13, 23: PRESSURE SENSOR
14, 24: DISPLAY UNIT
15, 16, 25: MEMORY
17: I/F
18, 28: OSCILLATION CIRCUIT
19, 29: POWER SUPPLY
21: PUMP
22: VALVE
26, 27: DRIVING CIRCUIT
51: AIR BAG
41 TO 44: SWITCH
101: INPUT UNIT
102: PRESSURE STORAGE UNIT
103: DETERMINATION UNIT
104: CALCULATION UNIT
105: THRESHOLD STORAGE UNIT
106: PATTERN STORAGE UNIT
107: DISPLAY PROCESSING UNIT
108: STORAGE UNIT

The invention claimed is:

1. A function adding device that connects to an electronic blood pressure meter, the function adding device comprising:
   a housing;
   a first connection portion that connects a first air tube;
   a second connection portion that connects a second air tube;
   a pressure sensor connected to an air passage comprising the first and second connection portions,
   wherein the pressure sensor is connected to the air passage through the housing, and
   wherein the air passage is connected to the electronic blood pressure meter at least with the first air tube interposed therebetween and is connected to an air bag at least with the second air tube interposed therebetween, the air passage, the electronic blood pressure meter, the first air tube, the second air tube and the air bag defining a closed space;
   at least one determination unit that, on a basis of a change in an internal pressure of the closed space that is detected by the pressure sensor, and on a basis of a pattern of a change in an internal pressure of an airbag that is associated with a permitted electronic blood pressure meter, the pattern stored in advance, determines whether or not the electronic blood pressure meter connected with the air passage is the permitted electronic blood pressure meter;
   a calculation unit that, on the basis of the change in internal pressure of the closed space that is detected by the pressure sensor, calculates a blood pressure value of a person to be measured to whom the air bag of the permitted electronic blood pressure meter is mounted; and
   a storage unit that stores the calculated blood pressure value,
   wherein the pressure sensor, the at least one determination unit the calculation unit and the storage unit are inside the housing.

2. The function adding module device according to claim 1, wherein the at least one determination unit on the basis of the change in the internal pressure of the air bag closed space detected by the pressure sensor, in a period of the change in the internal pressure of the air bag closed space, determines a period used for calculating the blood pressure value by the permitted electronic blood pressure meter, and
   wherein the calculation unit calculates the blood pressure value on the basis of the change in the internal pressure during the determined period from the change in the internal pressure of the air bag closed space detected by the pressure sensor.

3. The function adding device according to claim 2, wherein, in a case where an amount of the change in the internal pressure of the air bag is in a predetermined range stored in advance, the at least one determination unit determines that the period of the change in the internal pressure is the period used for calculating the blood pressure value by the permitted electronic blood pressure meter.

4. The function adding device according to claim 1, wherein the storage unit comprises:
   a storage area corresponding to a subject; and
   operation units that receive an operation of designating the subject to whom the air bag is mounted, and
   wherein the storage unit stores the calculated blood pressure value in the storage area corresponding to the designated subject.

5. The function adding module device according to claim 1, further comprising:
   a power supply inside the housing that supplies power to the function adding device; and
   a control unit inside the housing that, in a case where the change in the internal pressure of the air passage detected by the pressure sensor is equal to or greater than a predetermined amount that is stored in advance, performs control to supply the power to the function adding device from the power supply.

6. The function adding device according to claim 1, further comprising:
   a third connection portion that electrically connects to an external device; and
   an output that outputs information stored in the storage unit to the external device connected to the third connection portion.

* * * * *